US011793922B2

(12) United States Patent
Loske

(10) Patent No.: US 11,793,922 B2
(45) Date of Patent: Oct. 24, 2023

(54) VACUUM TREATMENT ARRAY AND FILM FOR PRODUCING A VACUUM TREATMENT ARRAY

(71) Applicant: LOHMANN & RAUSCHER GMBH, Schoenau/Triesting (AT)

(72) Inventor: Gunnar Loske, Ahrensburg (DE)

(73) Assignee: LOHMANN & RAUSCHER GMBH, Schoenau An der Triesting (AT)

(*) Notice: Subject to any disclaimer, the term of this patent is extended or adjusted under 35 U.S.C. 154(b) by 1211 days.

(21) Appl. No.: 16/143,828

(22) Filed: Sep. 27, 2018

(65) Prior Publication Data

US 2019/0060609 A1 Feb. 28, 2019

Related U.S. Application Data

(62) Division of application No. 14/429,545, filed as application No. PCT/EP2013/002839 on Sep. 20, 2013, now Pat. No. 10,188,830.

(30) Foreign Application Priority Data

Sep. 20, 2012 (DE) .......................... 102012018598.7
Dec. 6, 2012 (DE) .......................... 102012024001.5

(Continued)

(51) Int. Cl.
*A61F 13/00* (2006.01)
*A61M 27/00* (2006.01)
(Continued)

(52) U.S. Cl.
CPC ......... *A61M 1/84* (2021.05); *A61F 13/00068* (2013.01); *A61M 1/80* (2021.05);
(Continued)

(58) Field of Classification Search
CPC .. A61M 1/0023; A61M 1/008; A61M 1/0088; A61M 25/005; A61M 25/0066;
(Continued)

(56) References Cited

U.S. PATENT DOCUMENTS 3,394,702 A 7/1968 Heimlich et al.
5,512,045 A 4/1996 Gurchumelidze
(Continued)

FOREIGN PATENT DOCUMENTS

DE 10 2008 061 535 A1 6/2010
DE 102008061536 A1 6/2010
(Continued)

OTHER PUBLICATIONS

PCT Translation of the International Preliminary Report on Patentability dated Apr. 2, 2015 for priority PCT application, PCT/EP2013/002839 (14 pgs).
(Continued)

*Primary Examiner* — Benjamin J Klein
(74) *Attorney, Agent, or Firm* — Stinson LLP

(57) ABSTRACT

The invention relates to a vacuum treatment array having at least one open-pored contact element, by way of which a negative pressure and/or suction can be generated in a body cavity, wherein the open-pored contact element is configured, at least in sections, in the manner of a tube, having an outer and/or inner boundary surface rotating around a tube axis, at least in part.

9 Claims, 16 Drawing Sheets

(30) Foreign Application Priority Data

Dec. 27, 2012 (DE) .......................... 102012025388.5
Jan. 7, 2013 (DE) .......................... 102013000047.5

(51) Int. Cl.

| | | |
|---|---|---|
| A61M 1/00 | (2006.01) | |
| A61M 25/00 | (2006.01) | |
| A61M 25/09 | (2006.01) | |
| A61M 25/01 | (2006.01) | |

(52) U.S. Cl.

CPC .............. *A61M 1/916* (2021.05); *A61M 1/98* (2021.05); *A61M 25/005* (2013.01); *A61M 25/007* (2013.01); *A61M 25/0074* (2013.01); *A61M 25/09* (2013.01); *A61F 2013/0074* (2013.01); *A61M 27/00* (2013.01); *A61M 2025/0177* (2013.01); *A61M 2205/32* (2013.01); *A61M 2210/106* (2013.01); *A61M 2210/1064* (2013.01); *F04C 2270/0421* (2013.01)

(58) Field of Classification Search

CPC ............ A61M 25/007; A61M 25/0074; A61M 25/09; A61M 25/76; A61M 25/80; A61M 25/84; A61M 25/90; A61M 25/915; A61M 25/916; A61M 27/00; A61M 2025/0177; A61M 2205/32; A61M 2210/106; A61M 2210/1064; A61F 13/00068; F04C 2270/0421

See application file for complete search history.

(56) References Cited

U.S. PATENT DOCUMENTS

| | | | |
|---|---|---|---|
| 5,891,111 A | | 4/1999 | Ismael |
| 6,123,697 A | | 9/2000 | Shippert |
| 8,398,613 B1 | | 3/2013 | Hahn |
| 2001/0031943 A1 | * | 10/2001 | Urie ...................... A61M 27/00 604/47 |
| 2002/0161346 A1 | | 10/2002 | Lockwood et al. |
| 2003/0109855 A1 | | 6/2003 | Solem |
| 2005/0171467 A1 | * | 8/2005 | Landman ................ A61M 1/85 604/35 |
| 2006/0116691 A1 | | 6/2006 | Bonacci |
| 2007/0219497 A1 | * | 9/2007 | Johnson ................ A61M 27/00 604/131 |
| 2007/0282310 A1 | | 12/2007 | Bengtson et al. |
| 2009/0005750 A1 | | 1/2009 | West |
| 2009/0259203 A1 | | 10/2009 | Hu |
| 2010/0049166 A1 | * | 2/2010 | Koenig ................ A61M 27/00 604/385.01 |
| 2010/0160877 A1 | | 6/2010 | Kagan et al. |
| 2010/0179493 A1 | | 7/2010 | Heagle et al. |
| 2011/0270205 A1 | * | 11/2011 | Odermatt .......... A61F 13/15211 604/374 |
| 2011/0270301 A1 | | 11/2011 | Cornet |
| 2011/0319804 A1 | | 12/2011 | Greener |
| 2012/0071841 A1 | * | 3/2012 | Bengtson ................ A61M 1/84 604/319 |
| 2012/0123359 A1 | * | 5/2012 | Reed ...................... A61M 1/784 604/319 |
| 2012/0296207 A1 | * | 11/2012 | Chernomorsky ... A61M 31/005 600/431 |
| 2013/0023840 A1 | | 1/2013 | Loske |
| 2013/0035649 A1 | * | 2/2013 | Locke ...................... A61M 1/90 604/290 |
| 2013/0190706 A1 | * | 7/2013 | Kleiner ................... A61M 1/90 604/319 |
| 2015/0080861 A1 | * | 3/2015 | Ozer ...................... A61F 13/38 604/540 |
| 2015/0148785 A1 | * | 5/2015 | Kleiner ................ A61M 1/916 604/543 |

FOREIGN PATENT DOCUMENTS

| | | |
|---|---|---|
| DE | 102011013743 A1 | 9/2012 |
| EP | 2394677 A1 | 12/2011 |
| WO | WO 2003/028786 A2 | 4/2003 |
| WO | WO 2004/041346 A1 | 5/2004 |
| WO | WO 2011/038949 A1 | 4/2011 |
| WO | WO 2013/025285 A1 | 2/2013 |

OTHER PUBLICATIONS

PCT Search Report dated Mar. 7, 2014 for priority PCT application, PCT/EP2013/002839. (The original Search Report is in German. The original Search Report in German [6 pgs] and also an English translation [5 pgs] have been submitted for consideration.).

\* cited by examiner

VACUUM TREATMENT ARRAY AND FILM FOR PRODUCING A VACUUM TREATMENT ARRAY

CROSS-REFERENCE TO RELATED APPLICATIONS

This application claims priority to and is a divisional of U.S. patent application Ser. No. 14/429,545, filed on Mar. 19, 2015, which is a U.S. National Stage of International Application Number PCT/EP2013/002839 filed on Sep. 20, 2013, which published on Mar. 27, 2017 under International Publication Number WO 2014/04400, and which claims priority to German patent application 102012018598.7 filed on Sep. 20, 2012, German patent application 102012024001.5 filed on Dec. 6, 2012, German patent application 102012025388.5 filed on Dec. 27, 2012, and German patent application 102013000047.5 filed on Jan. 7, 2013, all of which are incorporated herein by reference in their entireties.

BACKGROUND OF THE INVENTION

The invention relates to a negative pressure treatment arrangement having at least one open-cell contact element, by way of which negative pressure and/or suction can be generated in a body cavity.

Conventional negative pressure treatment or vacuum therapy (low pressure wound therapy) is used for the treatment of external wounds. An open-cell polyurethane sponge or an open-cell fluid-collecting means is placed into the wound, sealed using a film, and then subjected to negative pressure. Under the film, assisted by the negative pressure, wound cleansing and wound healing can take place.

Endoscopic vacuum therapy or negative pressure treatment is used for the treatment of internal wounds. Its effectiveness was initially demonstrated in suture leaks at the rectum, and then also in intestinal leaks at other locations as well as in the area of the esophagus, the stomach, the small and large intestines. In the case of internal wounds, cavities, abscesses, empyema, fistulae or similar situated under the skin surface, which are or are made endoscopically accessible by way of an port outwards, endoscopic vacuum therapy can be used for wound treatment. In endoscopic vacuum therapy, the natural or artificial access routes to hollow organs, gastrointestinal tract and body cavities are endoscopically used.

Open-cell polyurethane foam drains are introduced using endoscopes internally, intracorporally, intraluminally and intracavitarily. In the intraluminal therapy variant, the sponge element is placed in an intestinal lumen at the level of the defect. In the intracavitary variant, the sponge element is introduced through the defect into an extraluminal wound cavity.

Within the scope of the specification of the invention herein, intraluminal regions as well as extraluminal regions are called body cavities.

The two above-mentioned therapies can also be combined. After positioning the sponge element, via the outward-conducted drainage tube, negative pressure or suction is applied. The body cavity (wound cavity or intestinal lumen) collapses subject to the suction, together with the elastic sponge element. The sponge surface adheres to the wound surface by suction, suction cup-like. As a result of the suction, at the same time, the sponge thus attaches itself also to the placement location. Effective wound drainage takes place. At the same time, the wound defect is closed. Subject to the lasting drainage effect and vacuum application to the wound surface, the wound is cleaned, granulation tissue forms, and secondary wound healing takes place. At intervals of several days, an endoscopic change of the drainage sponge is made.

Within the scope of the invention, a corresponding sponge drain is also referred to as contact element.

For placement of a sponge drain or a contact element in the rectum for the treatment of postoperative anastomotic failures, an approved placement system exists.

For placement of the contact elements or sponge drains in lower-lying regions of the body, such as the large intestine, the esophagus or the duodenum, having partially winding access paths, sponge drains are used, which comprise a drainage tube, to the end of which the contact element is sewn. The appropriate sponge element is grasped using gripping pliers, polyp grippers or slings and inserted subject to endoscopic direction.

For draining wound secretions, body fluids, suppuration and post-surgery, drainage tubes are inserted. They are tubes, into the inner lumen of which, through lateral perforations, secretions or gases can be drained. The drainage may take place as gravity drainage, overflow drainage, capillary drainage or subject to suction. Drains may also be designed as tubular drains or else as planar drains. Special drains, e.g. for bile congestion drainage, are also inserted surgically or endoscopically. Via drains, flushing can also take place. Drains can be subjected to negative pressure.

Wound drains usually develop their effect only immediately after an operation because fibrin precipitation, blood coagulation and tissue contact, inter alia, result in rapid clogging of the drainage ports. Whether drainage is possible also depends on the nature of the material to be drained. Feces, saliva or pus are viscous and require relatively large-lumen perforations, while urine, ascites, bile and the like are very flowable and can be drained by way of small-lumen ports, too.

Conventional drains consist of a tube, on which one or a plurality of lateral perforations are located. The ports communicate fluid-conductively directly with the inner lumen of the drain.

For an open-cell sponge drain or an open-cell contact element, a drainage tube equipped with perforations is introduced into an open-cell sponge. The drainage tube is fluid-conductively connected, via the perforations, to the open-cell fluid-collecting element. The sponge acts like a filter. As a result of the open-cell sponge structure, when a negative pressure is applied, the sponge surface can adhere to a wound or the wound margins by suction over a large area. The cell ports of the sponge act like little suction cups. As a result of the open-cell structure of the fluid-collecting means or the contact element, the numerous perforations communicate with each other fluid-conductively. This assures the maintenance of an applied negative pressure to the adjacent wound surface, even when individual cells are clogged. Even though a secretion can only be suctioned off by way of a small surface, this drainage is also assured by the open-cell communication of the numerous cells with each other. This is a substantial difference from the conventional drainage tubes, where a tube has individual perforations. Once these ports are clogged, because of the missing connection between the individual perforations (except by way of the inner lumen of the tube) any suction and drainage effect is interrupted.

EP-A-12001013.7 describes a negative pressure treatment arrangement, in which the contact elements are formed by two open-cell drainage layers. The cells of the open-cell drainage layers communicate with each other by way of the drainage space situated in between. Between the two drainage layers, a suction arrangement, connectable to a suction device, for suctioning off any exudate that gets between the drainage layers is arranged. To promote wound healing, the suction arrangement of this prior art negative pressure treatment arrangement has a flushing arrangement for supplying a fluid between the drainage layers allocated to it. Through the flushing arrangement, a fluid flows into the body cavity. As a result, the flow in the suction arrangement is continuously maintained. Coagulations are avoided because bottom exudate is continuously suctioned off by the suction arrangement toward the suction device.

By reference thereto, the disclosure content of the document herein is expressly incorporated into specification herein with respect to the embodiment of the drainage layers and the suction device or flushing arrangement arranged between the drainage layers.

When using conventional negative pressure treatment arrangements of the type described above, in many cases, the placement, also and especially including the endoscopic placement, as well as the removal of the contact element at or from the treatment site in the body cavity causes problems.

BRIEF SUMMARY OF THE INVENTION

In view of these problems in the state of the art, the invention is based on the objective of providing a negative pressure treatment arrangement, which can be arranged at a treatment site in a body cavity without any problem and be also removed again from this treatment site, as well as a film for producing a corresponding contact element.

According to the invention, this objective is achieved by an enhancement of the prior art negative pressure treatment arrangements, which is essentially characterized in that, at least in sections, the open-cell contact element is embodied tubular, having an outer and/or an inner boundary surface that at least partially encircles a tube axis.

According to the invention, with respect to its shape and features, the contact element, which may, for example, instead be embodied as a fluid-collecting element for collecting fluids or gases, may be adapted to the drainage tube required for the application of the negative pressure and for the outward-conducting of body fluids and gas. It may be embodied in such a way that, with respect to the tube axis, it does not radially extend beyond the drainage tube. In this case, it can be introduced into the body cavity without any problems and also be removed from it again.

In other embodiments of the invention, in the area of the contact element or fluid-collecting element, the drainage tube may widen, continuous widening for the purpose of simple introduction of the contact element into the body cavity or removal from it having proven to be particularly advantageous. The contact element, embodied as a fluid-collecting element, may be connected fluid-conductively to a channel-shaped lumen of a drainage tube in such a way that a tubular drain is created, in which the open-cell fluid-collecting element as part of the tube wall and the drainage tube forming a fluid-communicating element are structurally interconnected.

Overall, the invention is based on the following knowledge:

Endoscopic placement as well as removal of an open-cell polyurethane sponge sewn to a drainage tube can be problematic due to the size of the polyurethane sponge as well as its volume and its diameter.

As a result of the incongruity of the diameters of the fluid-collecting means or polyurethane sponge serving as contact element and the fluid-communicating element or drainage tube, placement and removal of the drain may be difficult.

The placement and particularly also any accidental uncontrolled removal of a conventional negative pressure treatment system being used in the upper gastrointestinal tract with outward-conduction from mouth or nose may cause airway obstruction and, therefore, result in a life-threatening situation for the patient.

For placement and removal of a drain, it is advantageous if the fluid-collecting means, or contact element, and the fluid-communicating element, or drainage tube, have the same diameters and continuously merge into each other.

The drainage action effectiveness of a negative pressure drain does not depend on the volume of the contact element or sponge element. Instead, using a sponge element many times smaller compared to the wound cavity or body cavity to be treated, wound healing that is equally good as with a contact element adapted to the size of the body cavity can be achieved because a small sponge element may suffice for draining a large wound and the wound with the sponge element collapses subject to the suction above the sponge element. Related thereto, it also became obvious that the wall of a drainage tube can be produced as an open-cell contact element or fluid collecting element, the open-cell wall area of the drainage tube or the wall area of the drainage tube formed by the contact element needing to be only a few millimeters thick to allow its use as a vacuum sponge drain. The drainage tube or parts of the drainage tube can be provided with a curvature (pigtail).

In contrast to a sponge sewn to a drainage tube having become firmly attached by suction to a wound during the negative pressure treatment, there is hardly any chance any more for a contact element embodied according to the invention, when removed from the body cavity, to tear away from the drainage tube. Within the scope of the invention, various types of open-cell fluid-collecting elements can be combined with each other, allowing the placement of the drains and the therapy using specially equipped drains and accessories to be simplified.

The invention results in numerous new therapy options and applications, which are particularly exploitable in wound treatment and in surgery complication management. Particularly, when using negative pressure treatment arrangements according to the invention, in which contact element and communication element are structurally combined in one drainage tube, the life-threatening risk of airway obstruction, which is especially liable to occur in a case of accidental removal or dislocation during application in the upper gastrointestinal tract, is prevented.

BRIEF DESCRIPTION OF THE DRAWINGS

FIG. 1b is a cross-sectional view of FIG. 1a.

FIG. 8a is a longitudinal sectional view of the transition from fluid-collecting segment 1 to fluid-communicating element 2.

FIG. 8b is a longitudinal sectional view of the transition from fluid-collecting segment 1 to fluid-communicating element 2.

FIG. 8c is a longitudinal sectional view of the transition from fluid-collecting segment 1 to fluid-communicating element 2.

FIG. 8d corresponds to the longitudinal sectional view in FIG. 8c.

FIG. 8e corresponds to the longitudinal sectional view in FIG. 8d.

FIG. 8f corresponds to the cross sectional view of a drain having four tubular film layers 9, 9c, 9d, 9f and being provided with central fluid-conductive channel 4a.

DETAILED DESCRIPTION OF PREFERRED EMBODIMENT

Figure 1A:
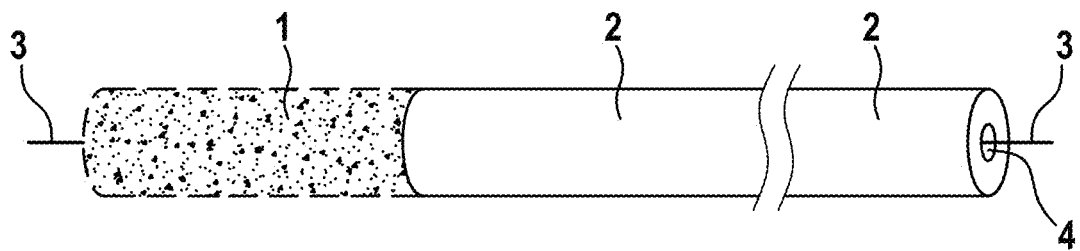
FIG. 1a is a representation of a negative pressure treatment arrangement according to the invention in the form of an open-cell drainage tube.

In a preferred embodiment of the invention, a tubular drain is used, which structurally combines in itself the fluid-collecting element (contact element) and the fluid-communicating element of the drain. As a particular advantage, negative pressure treatment arrangements according to the invention can be used within the framework of endoscopic vacuum therapy. Appropriate arrangements can also be used for intraabdominal, thoracic drainage after surgery, in wound treatment, relief of abscesses and during wound healing problems. In particular, a negative pressure treatment arrangement according to the invention can be used in intestinal anastomoses prophylaxis and in the treatment of anastomotic insufficiencies and intestinal perforations. The range of applications is very wide.

The fluid-communicating element, which, according to a preferred embodiment of the invention, is structurally combined with the fluid-collecting element, will hereinafter be referred to as fluid-communicating collection element and abbreviated "FE". In an FE according to the invention, flexible negative pressure-stable drainage tubes may be involved, in which the wall or portions of the tube wall are designed as open-cell contact elements or fluid-collecting elements. Thus, by means of the open-cell contact elements as constituent parts of the drainage tubes fluids or gases can be drained.

The FE is fluid-conductive and equipped with open-cell fluid-collecting segments or contact elements, which consist of the wall or parts of the wall of the FE. It is particularly advantageous to have the open-cell fluid-collecting segments of the FE located at the distal end of the tube. The open-cell fluid-collecting segment or contact element may instead be located in a section between the proximal or distal end of the tube. In this embodiment of the invention, the fluid-collecting segment is expediently located in the central portion of the FE.

The FE may be provided with only one or else two, three or a plurality of fluid-collecting segments or contact elements. Fluid-collecting segments or contact element—elements may have a length of a few mm to several cm. When specially indicated, e.g. when complete evacuation of the stomach or other long intestinal stretches is necessary or for securing and covering a defect in the esophagus, fluid-collecting element portions or open-cell contact elements having a length of more than 20 cm, esp. 30 cm or more, are used. The drain is also especially suitable for the additional securing of a critical anastomosic situation at sutures in the entire gastrointestinal tract to prevent post-surgery anastomotic insufficiency.

The fluid-collecting element or contact element may consist of an open-cell elastic compressible polyurethane sponge element. Preferably, the contact element will have a cell size of 200 μm to 1000 μm, esp. 400 μm to 600 μm. The fluid-collecting element or contact element may instead be formed of a one-, two- or multilayer open-cell film or be provided with such a film. Corresponding films are described in EP 2 427 477 A. By express reference thereto, the disclosure content of this document is hereby incorporated in the specification herein with respect to the embodiment of open-cell multilayer films.

Within the scope of the invention, the use of a combination of an open-cell polyurethane sponge element and an open-cell film for obtaining an open-cell fluid-collecting element or contact element is also intended. The fluid collecting element may consist of an open-cell plastic material. Preferably, polyurethane, polyvinyl and polyethylene will be used as materials for the FE. If the fluid-collecting segment or contact element is externally covered by an open-cell film, it has the purpose of improving the slidability of the FE. The design with open-cell films as contact elements also allows a structure having a minimal diameter accompanied by good fluid conduction. Moreover, the furnishing with films increases the tensile strength of the FE.

The contact element embodied as a fluid-collecting element is expediently connected fluid-conductively to the fluid-communicating element or drainage tube. The fluid-communicating element preferably consists of a drainage tube having a central fluid-conductive channel, which is conducted onward as a tube into the fluid-collecting element or contact element and is fluid-conductively connected here, by way of lateral ports, to the open-cell fluid-collecting element, which is part of the wall of the fluid-communicating element. The fluid-communicating element or drainage tube preferably consists of a tube having a central channel and additional channels, which are located in the wall of the FE and which are also fluid-conductively connected to the fluid-collecting segment or contact element. The fluid communication element may consist of a tube having a plurality of channels or lumens.

The fluid-communicating element may have a drainage tube, which is embodied by a plurality of fluid-conductive channels. The fluid-conductive channels may be equilumenous or have different lumens. The channels may be fluid-conductively interconnected. The channels of the fluid-communicating element may be used for suctioning and flushing. Into the channels, a guide wire, measuring probes or instruments can be introduced. As far as their lengths and arrangements in the FE are concerned, the channels may be dimensioned in such a way that individual channels are connected to individual fluid-collecting elements or contact elements. One or a plurality of channels in FE may also be designed in such a way that they extend several centimeters or decimeters beyond the FE per se and/or can be used as feeding probe. This is a particular advantage in the intraluminal application of the probe in the upper gastrointestinal tract.

In a preferred embodiment of the invention, a guide wire may be introduced into the FE, by way of which the FE can slide. The FE can have an overall length of 80 cm to 250 cm.

Because during a pull-through maneuver or a removal maneuver, the tensile strength exerted on the FE is not insubstantial, it is preferably designed traction-resistant and break-resistant so that it cannot be torn off. Preferably, a tensile strength of 50 N, esp. 100 N, expediently of up to 200 N must exist. The FE should also be radiopaque. Within the scope of the invention, it has proven to be expedient if the FE cannot be kinked against itself because kinking disrupts the onward conduction of negative pressure or the evacuation of secretions.

The FE that is conducted out of the body cavity may be connected, by way of connecting elements, to a negative pressure generating system, esp. an electronic vacuum pump. If both the proximal and the distal leg of the fluid-communicating element are conducted outward, a negative pressure or suction may be applied at both the distal and/or the proximal end. Negative pressures in the range between 40 mm Hg and 200 mm Hg will be used. In the thoracic application, lower negative pressures will also be used.

Preferably, an FE according to the invention will have an outer diameter of 2 mm to 20 mm. In a particularly preferred embodiment of the invention, a drain equipped with an open-cell contact element according to the invention and having small-diameter can be endoscopically placed by way of the working channel of an endoscope. Expediently, all sections of the FE will have the same outer diameter. The open-cell fluid-conductive fluid-collecting segment(s) or contact element(s) of the drain preferably merge continuously into the fluid communication sections. This makes it possible to transnasally introduce a negative pressure treatment arrangement according to the invention when used in the upper gastrointestinal tract. With prior art arrangements, this is not possible. Moreover, the negative pressure treatment arrangement according to the invention can be more easily removed by pulling if the diameter of the contact element is adjusted to the diameter of the drainage tube without any mechanical obstruction due to the contact element design. This allows the use of a negative pressure treatment arrangement according to the invention as a cutaneously outward-conducted target drain during surgery or for fluid drainage in all body cavities. Negative pressure treatment or vacuum therapy can be used in these locations and removal of the drain is possible without any new surgical intervention.

By way of the FE, within the scope of the invention, a flushing treatment can also be carried out. In particular, in case of placement of the FE in the central section and outward conducting of both fluid communication legs or drainage tubes, one of the legs can be used for suction and the other for flushing.

Into the wall of the FE, in the longitudinal direction, wires or threads can be incorporated, by means of which stability and/or tensile strength of the FE can be increased and, as a result, tearing off of the FE can be prevented.

The distal end of the FE is expediently conical in its design, terminating in a point. This facilitates the drain placement maneuver. As a particular advantage, the conical point of the drain will be soft and atraumatic in its design, in order to avoid injury to adjacent tissue.

At the distal end of the fluid-communicating element or drainage tube, at the fluid-collecting element or contact element or in the fluid-collecting element, advantageously, a device will be attached, which can be grasped using pliers, hooks, sling or another placement instrument. In particular, a thread or wire loop may be attached. Particularly preferred, a metal or plastic gripping bead may be provided. In particular, a metal or plastic eyelet may be attached. A thread may also be attached. These devices are preferably designed traction-resistant so that the drain or negative pressure treatment arrangement on these elements can be drawn through tissue, intestinal lumina and fistulas. The devices are designed to be flexible and atraumatic.

The placement of a negative pressure treatment arrangement according to the invention can be implemented using a placement instrument in an orthograde manner subject to endoscopic vision. In the presence of an additional outward connection, using the placement instrument or the fixed thread, placement can also be performed applying the pull-(through) technique. The change maneuvers can be greatly simplified by using the pull-through technique.

In the embodiments of the invention hitherto described, the open-cell contact element of the negative pressure treatment arrangement according to the invention will be used in conjunction with a drainage tube for draining fluids or gases from a body cavity. Additionally or alternatively, the negative pressure treatment arrangement may comprise a tubular hollow body for medical applications in the human or animal body, its outside being provided with the contact element, wherein the contact element consists of a gas and fluid-impermeable film or membrane, its outward-facing side having an open-cell surface, along which fluids and/or gases flow, and its inward-facing side preferably having an open cell-free fluid and/or gas-tight surface.

Intestinal wall defects and airway leaks can entail the most serious disease patterns. Despite complex surgical procedures and intensive medical treatment, they are encumbered by high mortality rates.

For bridging and sealing defects in the gastrointestinal tract, as an alternative to surgical therapy, self-expanding metal and/or plastic stents are in use. For this purpose, the stents can be fully or partially covered using a gas and/or fluid-impermeable film coating. They are then referred to as covered stents. The covering achieves a fluid and gas-tight barrier between the inner lumen and the stent exterior. In principle, the structures involve self-deployable hollow bodies or tubes, which are placed by means of a set of placement instruments.

Likewise, for sealing of defects, tubes are used that, in principle, consist of plastic pipes, both ends of which are open. Stents and tubes are also used for bridging lumen-obstructing obstacles, such as cancerous tumors. Sealing by a covered stent is caused when the stent deploys and its outside is pressed against the intestinal wall. A disadvantage of stents is the deficient sealing in case of a lumen incongruity. Such a condition always exists when, during intestinal surgery, various lumens are linked by a suture. This occurs, for instance, in the case of a sutured connection of esophagus and stomach. If, in this area of the suture, e.g. in the transition from esophagus (small lumen) and stomach (large lumen), a leak exists, sealing by deployment of a stent is usually not complete. This situation frequently arises in anastomosis situations. This may complicate the treatment of postoperative leaks using stents and tubes. The stent deploys after release and is supposed to press against the intestinal wall and become anchored in it and provide sealing against the mucous membrane in doing so, while a tubus can only achieve a bridge along the course of the lumen, without exerting any outward expansion pressure.

Another problem of stents and tubes is their dislocation. It occurs if the hollow bodies cannot become sufficiently anchored in the intestinal wall.

Another complication of stents and tubes is the perforation as a result of the hollow body located in the intestinal lumen, through the wall from inside outward. Perforations occur particularly on the funnel-like flare of the tubular hollow bodies.

A new possibility for treating leaks, e.g. on the esophagus, the stomach or caused by excessive distention, but also at the rectum, consists in the method of endoscopic negative pressure treatment or vacuum therapy. For this purpose, open-cell polyurethane foam drains are inserted by intracavitary and intraluminal endoscopy and subjected to negative pressure by way of a drainage line. The suction effect causes the attachment of the sponge element by suction to the intestinal wall, with sealing of the covered defect and induction of a secondary wound, which can then heal by itself.

According to this aspect of the invention, it is proposed to combine the technical advantages of vacuum therapy with a stent or tubus using a unilaterally open-celled film or a unilaterally open-celled contact element. In doing so, the disadvantages in the scope of the invention described above are eliminated or corresponding problems are solved. Patient safety is increased by avoiding stent-caused complications and the indication range of the therapy is expanded. Numerous new therapeutic options are opened, and esp. in the management of surgical and endoscopic complications, tent and tubus can be used. The application should be possible in the human and the animal body.

In accordance with this aspect of the invention, the jacketing of a self-expanding metal and plastic mesh stent is carried out using an open-cell contact element in the form of a unilaterally open-celled film, the shape of the film being used as contact element corresponding to the shape of the stent or tubus being embodied at least partially encircling a tube axis. The special film forming the contact element may consist of a gas and fluid impermeable membrane. This membrane has two sides, which differ from each other in their characteristics.

One side of the membrane is open cell-free. This side will be situated on the metal mesh wires or the plastic mesh of the stent and will be structurally connected to it. The contact element embodied by the film can be permanently connected to the wires or the mesh by gluing and/or welding. The film forms the inside of the tubular hollow body, both ends of which are open.

The other side of the membrane is embodied by the outside of this tubular hollow body. It has an open-cell surface. This surface is characterized in that, along this film side and/or this side of the contact element, gases and fluids can freely communicate, move and flow. As a result of the open-cell surface structure, the film or the contact element on this side has the characteristics of a fluid-collecting element. This open-cell side of the surface can be subjected to negative pressure. When the negative pressure is applied to this side, as a result of the open-cell structure, suction directed toward the negative pressure source becomes possible across the entire open-cell film surface. This open-cell film side or this open-cell contact element side comes into contact with the surrounding tissue and, as a result of negative pressure, adheres to the tissue.

In this way, the inadequate sealing of conventional covered stents, such as in the case of incongruity of intestinal lumens, can be compensated. The outside of the stent adheres to the intestinal wall like a suction cup by means of the (unilaterally) open-cell contact element subject to suction. In this way, the stent is fixed to the placement site, preventing dislocation, which is a typical complication when using conventional stents. Experience has shown that draining major amounts of fluid by means of the negative pressure is not what matters but what does matter is producing an intimate connection by means of the suction between the intestinal wall and the stent.

Preferably, in the proximal and/or distal peripheral area of the contact element or the film jacketing, the open-cell outside merges into an open-cell-free surface structure, so that, as a result, in the peripheral area of the film, a boundary that is not fluid-conductive is created. This facilitates the development of negative pressure applied to the open-cell surface. The open-cell structure of the film side or contact element side can be achieved by a differing design of the surface structure of the open-cell film side. The open-cell structure can, for instance, be achieved by mesh, nub, finger or channel-shaped structures. The cell size should be between 200 μm and 1000 μm. The negative pressure is preferably generated by means of an electrically controllable pump. The negative pressure can, however, instead be generated by means of a vacuum bottle. According to knowledge obtained from endoscopic vacuum foam therapy, the necessary negative pressure is preferably between 40 mm Hg and 200 mm Hg.

The negative pressure can be transferred using a fluid-communicating element, which preferably consists of one or a plurality of negative pressure-stable tubes, which are fluid-conductively connected to the open-cell side of the contact element. The fluid-communicating element may be branched fan-like or root-like on the open-cell film side. Thus, the suction action on the entire surface side can be optimized. The fluid-communicating element may be designed removable, i.e. it may be detachable from the tubular hollow body (tubus or stent), so that the stent can be used even without any negative pressure application. As a result of the removability, it is possible to perform the vacuum or negative pressure treatment during the first therapy days and then to terminate suction while still leaving the stent in the treatment site. Due to this property, it is possible to vary the configuration of stents. A typical stent configuration is the tulip-shaped, funnel-like outward port of the lumen. This intends to achieve improved sealing and anchoring of the stent on the wall.

Complications frequently observed in the use of stents are perforations by these tulip-shaped extensions. In a stent equipped according to the invention, having a unilaterally open-celled surface, adhesion to the wall is assured by the negative pressure, so that the funnel shape can be minimized. In a preferred embodiment of the invention, the funnel shape is completely omitted. This increases substantially the patient safety when using stents in the gastrointestinal tract. Stent-related complications as a result of perforations and dislocations can be prevented. At the same time, the efficacy of the stent is optimized. In this aspect of the invention, the contact element is expediently embodied as a film. The film can be thin-walled and/or elastic and/or flexible and/or transparent.

Within the scope of the use of tubular hollow bodies having open-cell contact elements according to the invention, the application of the vacuum or negative pressure therapy on the bronchial system in cases of tracheal or bronchial injuries becomes particularly possible, without being limited thereto. This creates completely new therapy options for these hard-to-treat disease patterns. The application of endoscopic vacuum therapy is hitherto not possible for this indication. It is conceivable that it will become possible to avoid numerous surgeries by the use of this novel treatment option.

The preceding statements apply equally to a tubus, which consists of a bilaterally open plastic tube, the outer surface of which is enclosed in a tubular jacket by means of a unilaterally open-celled film or a unilaterally open-celled contact element.

A special embodiment of a unilaterally open-celled tubus is an overtube-tubus for endoscopes. The overtube can advantageously be provided with a complete longitudinal slit.

A particular embodiment of a unilaterally open-celled tubus is a single or dual lumen endotracheal intubation tubus. As an alternative or in addition to tracheal sealing, subject to negative pressure suction, the tubus can endotracheally become attached by suction to the tracheal wall by way of one or a plurality of open-cell circular tubus segment(s).

A film according to the invention used to produce an open-cell contact element of a negative pressure treatment arrangement according to the invention is essentially characterized in that it consists of a gas and fluid-impermeable membrane, one side of which has an open cell-free surface and the other side of which has an open-cell surface, along which fluids and/or gases can flow. The open cell-free surface of a film according to the invention may be at least partially designed to be smooth. Additionally or alternatively, it may also have textured surface areas. In particular, this surface may be provided with a groove-like profile or a mesh profile.

The other side of the film has an open-cell structure. The open-cell structure of this surface is characterized in that fluids or gases can freely move along this surface in all directions and communicate with each other. When the open-cell surface side is placed on a body tissue, fluids and gases can move through the open-cell structure between the tissue surface and the film surface side. Negative pressure can be applied in the interstice between the tissue and/or to the open-cell surface side. A directed negative pressure can be applied in the space. This means that the fluids or gases can be aspired by one or a plurality of negative pressure sources and move in the direction of these sources. Along this space of the open-cell surface side of the film, fluids and gases can flow directed by a negative pressure. Fluids and gases can likewise be introduced into this space in the opposite direction from the outside. For example, a liquid medication can be supplied. The open-cell surface side can act as a medication carrier and be loaded with special substances, such as antiseptics. By means of an applied negative pressure, this film side can adhere by suction over a wide area of the entire surface of body tissue or other closed surfaces. The open-cell structure remains intact upon application of the negative pressure.

The open-cell structure of the surface is a structural part of the film per se. The film combines in itself the open-cell structure and the open cell-free structure or impermeability on the other side.

The open-cell structure is achieved by an open-cell surface structure of the film per se. The open-cell surface structure can be particularly achieved using an open-cell mesh-type surface structure. It can be achieved by a nub-like and/or villus-shaped structure or a combination of different surface patterns.

The open-cell structure of the surface can be achieved by applying an open-cell material to the membrane, for instance. The surface can, in particular, be loaded with a thin layer of an open-cell fluid-collecting element. The fluid-collecting element can, in particular, be loaded with a layer of open-cell polyurethane foam.

The open-cell structure of one of the film sides can also be achieved in that the film on the open-cell side consists of open-cell dual or multilayer perforated films, for example according to EP-A-2424477. With respect to each other, these multilayer films are spaced in such a way using spacers that the membranes do not have any direct areal contact with each other. The film membranes of the multilayer open-cell films are provided with a plurality of small perforations. These perforations may be arranged in an ordered pattern or they may instead be irregularly distributed.

In the case of a multilayer film layer, the films in the peripheral area of the film can advantageously be welded to each other without being fluid-conductive, so that fluid conduction beyond the edge is not possible. In the case of a single-layer unilaterally open-celled film, advantageously both film sides bilaterally merge into an open cell-free surface structure of the film side. As a result, the unilaterally open-celled film is not fluid conductive in the peripheral area.

Depending on the application, the peripheral area may be provided with an adhesive on both the smooth open cell-free side and the open-cell side. In this way, the film can be glued to a wound like a band-aid, sealing and closing it.

As a result of the fluid-conductive connection to a fluid-communicating element, which is fluid-conductively connected to the open-cell film side, using a negative pressure-generating system, e.g. an electronic pump or a vacuum bottle, negative pressure can be generated on the open-cell film side. The fluid-communicating element may consist of tubular drainage lines. The tubular fluid-communicating elements may be integrated in the film and be fluid-conductively connected to the open-cell film side. The fluid-communicating elements may be branched capillary-like on the open-cell surface. Moreover, the closed film side can also be opened to be fluid-conductive and, by way of this port, the fluid-communicating element can be fluid-conductively connected to the open-cell film side. This can be achieved by a fluid-conductive pelotte, which is glued to the film.

In a preferred embodiment of the invention, the peripheral area may also have a fluid-conductive open-cell structure. This may, for example, be advantageous when applied in the open abdomen when the film is used to enclose an organ (e.g. the spleen or liver) and to subject its open-cell side to negative pressure. In this case, the peripheral area of the film will be closed, too, by the aspiration of tissue. Because in this application no closed peripheral area is necessary, the film can be freely cut to size and adapted to the requirements. Because the film is unilaterally open-celled, the suction action is deployed only on this side, while the organs abutting the closed side are not subjected to the suction. This avoids damaging the organs that do not require any treatment by the negative pressure. This is a particular advantage.

The film is, in particular, foldable and/or soft and atraumatic and/or elastic and/or transparent and/or not transparent and/or colored. The film can be sewn, welded and glued.

The film thickness is preferably from 0.5 mm to 5 mm. If the film is used to equip a medical device, e.g. a self-expanding stent, an even lower film thickness can be selected so that the stent can be compressed to the smallest possible size.

The film can be fluid-conductively connected together with other fluid-collecting elements. It can, for example, be used as film in an occlusive dressing or in low-pressure wound therapy on external wounds.

The film may be folded or rolled into a multilayer film. In conjunction with a fluid-communicating element, it can be used as an active negative pressure film and/or an active film.

The film may be adapted to different body shapes. A glove or a face mask can, for instance, be made from the film, so that a wound dressing adapted to the shape of the body can be put on like a garment.

In the peripheral area, the film is advantageously provided with an adhesive means, so that the dressing can be adhered to the skin.

By way of a fluid-communicating element, which is fluid-conductively connected to the open-cell side of the film, negative pressure can be applied to the wound or skin.

The negative pressure generates both a suction effect and a pressure effect on the abutting tissue. As a result of the negative pressure, the wound secretion that is typically present at a wound is drained so that the wound is drained subject to slight compression.

It is particularly preferred to have the film designed transparent so that the evaluation of a surface wound can be carried out through the dressing. If the film is loosely placed on a skin surface or a wound and is elastic, the applied negative pressure draws it all the way to the tissue surface and adjusts to it.

Another typical application example is the wound care after skin transplantation.

Using a film according to the invention, in particular including medical instruments or therapeutic devices can be technically equipped. Advantageously, it can be used in the areas where, on the one hand, a fluid- and/or gas-tight boundary to an appliance or tissue is desired and, on the other hand, drainage of fluids or gases along the film is advantageous. Depending on the requirements, in this case, one as well as the other film side may be advantageous in use. In this respect, it is particularly advantageous that the thin-walled film does not cause any substantial increase in the film-loaded unit.

As explained in detail above, so-called covered self-expanding stents that are used for treating leaks in the gastrointestinal tract, can be equipped with open-cell film. If the film is used here as cover film on the stent (open-cell side toward the tissue, smooth closed side toward the stent), conventional stent bridging by applying vacuum suction to the abutting tissue is simultaneously possible.

Particularly advantageous would be such use in the case of a lumen incongruity of the intestinal lumens to be bridged or in the bronchial system. In the same way, tubes, overtube, probes, endoscopes, which are introduced intracorporeally, can be enclosed in an open-cell wrap. If the closed side is situated on the device side, the simultaneous application of the vacuum to the tissue and use of the vacuum therapy is possible. If the open-cell side of the film is placed on the medical device, this arrangement can serve as a protective enclosure for the medical device. As a result of the suction, the film terminates at the device and does not substantially contribute to any increase in circumference.

Advantageously, the outfitting of ventilation tubes and anesthesia tubes is also possible. Here, hitherto, sealing of the tubus vis-a-vis the trachea using a balloon has been taking place. If, in this case, the tubus is equipped with a unilaterally open-celled film, sealing can be achieved by way of the vacuum. In the case of all medical instruments, in which fixation is performed by balloon expansion, fixing and sealing may also take place by vacuum suction. Another example of outfitting devices is the use of the film in vacuum endoscopy as an endoscopic examination method for the small intestine. In analogy to single or dual balloon endoscopy, fixing of the overtube and the endoscope can take place by suction.

Hereinafter, the invention will be explained with reference to the drawing, to which express reference is made with respect to all details that are essential to the invention and not highlighted in detail in the specification.

FIG. 1a is a representation of a negative pressure treatment arrangement according to the invention in the form of an open-cell drainage tube. Open-cell fluid connection segment 1 or contact element 1 is located at the distal end of tubular fluid-communicating element 2. A guide wire 3 is inserted into a channel 4.

Figure 1B:
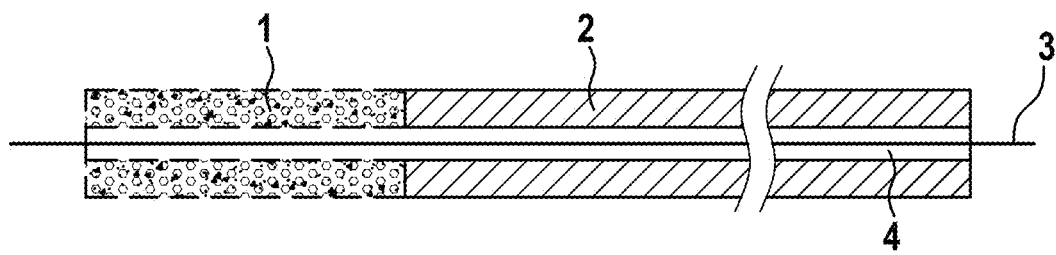

FIG. 1b is a cross-sectional view of FIG. 1a. Fluid-collecting segment 1 and fluid-communicating element 2 continuously merge into one another. Into both, by way of a channel 4, guide wire 3 is inserted. Channel 4 is fluid-conductively connected to fluid-collecting segment 1 or contact element 1.

Figure 1C:
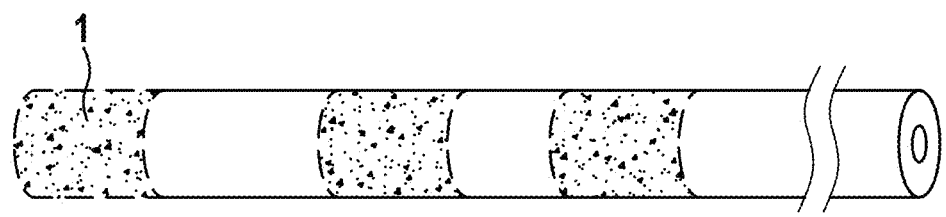
FIG. 1c is a representation of an open-cell drainage tube having a plurality of open-cell fluid-collecting segments 1 or contact elements 1.

FIG. 1c is a representation of an open-cell drainage tube having a plurality of open-cell fluid-collecting segments 1 or contact elements 1.

Figure 2A:
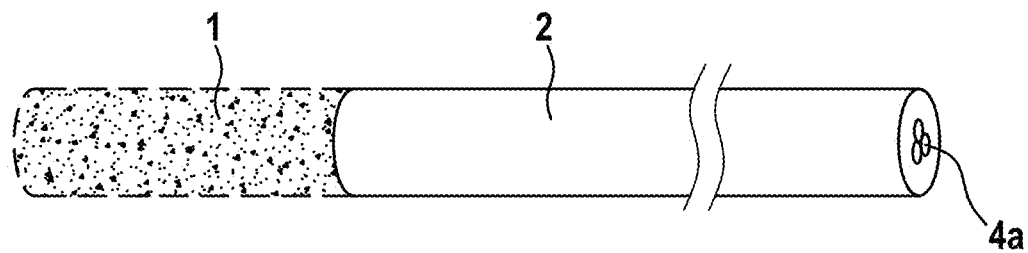
FIG. 2a is a representation of an arrangement according to the invention in the form of an open-cell drainage tube.

FIG. 2a is a representation of an arrangement according to the invention in the form of an open-cell drainage tube. The open-cell fluid-collecting segment 1 or contact element 1 is located at the distal end of tubular fluid-communicating element 2. In fluid-communicating element 2, a three-lumen channel 4a is arranged.

Figure 2B:
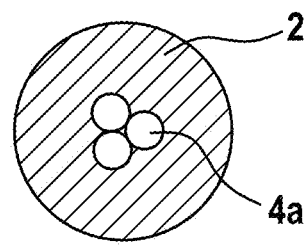
FIG. 2b is a cross-sectional view of FIG. 2a at the level of fluid-communicating element 2.

FIG. 2b is a cross-sectional view of FIG. 2a at the level of fluid-communicating element 2. Centrally, a three-lumen channel 4a exists.

Figure 2C:
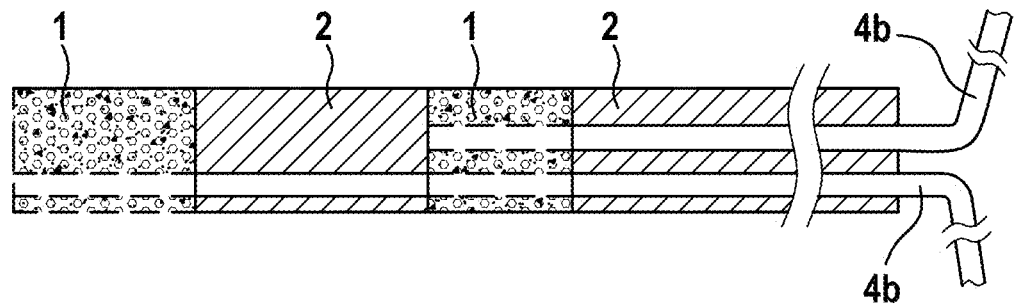
FIG. 2c is a longitudinal sectional view of an open-cell drainage tube having two fluid-collecting segments 1.

FIG. 2c is a longitudinal sectional view of an open-cell drainage tube having two fluid-collecting segments 1. Each fluid-collecting segment 1 or contact element 1 is fluid-conductively connected to a channel 4b, which through fluid-communicating element 2.

Figure 3A:
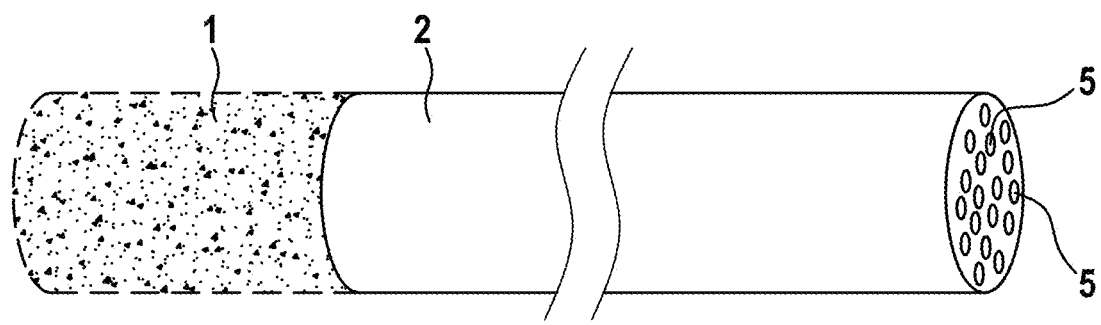
FIG. 3a is a representation of an open-cell drainage tube.

FIG. 3a is a representation of an open-cell drainage tube. Open-cell fluid-collecting segment 1 or contact element 1 is located at the distal end of tubular fluid-communicating element 2. In fluid-communicating element 2, a plurality of small-volume channels 5 is located, which extend fluid-conductively as far as fluid-collecting segment 1.

Figure 3B:
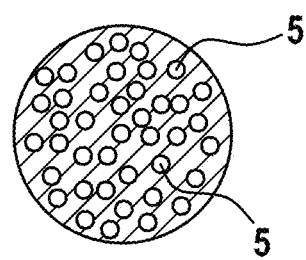
FIG. 3b is a cross-sectional view of FIG. 3a at the level of fluid-communicating element 2, which is provided with a plurality of channels 5.

FIG. 3b is a cross-sectional view of FIG. 3a at the level of fluid-communicating element 2, which is provided with a plurality of channels 5.

Figure 4:
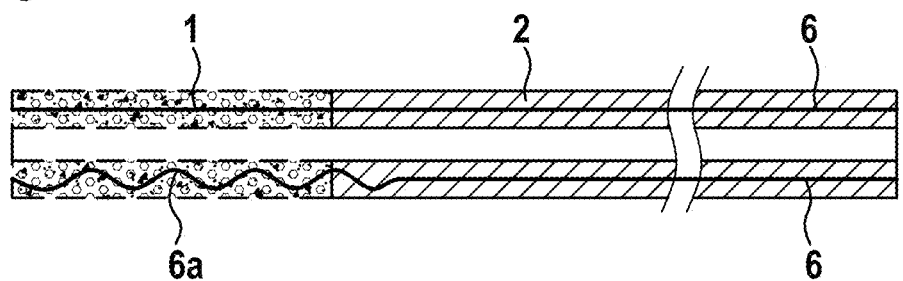
FIG. 4 is a longitudinal sectional view of an arrangement according to the invention in the form of an open-cell drainage tube.

FIG. 4 is a longitudinal sectional view of an arrangement according to the invention in the form of an open-cell drainage tube. Open-cell fluid-collecting segment 1 or contact element 1 is located at the distal end of tubular fluid-communicating element 2. In the wall of the tube, for increasing the tensile strength of the wall, a wire-shaped thread 6 is located. It may also meander and run in winding curves 6a.

Figure 5:
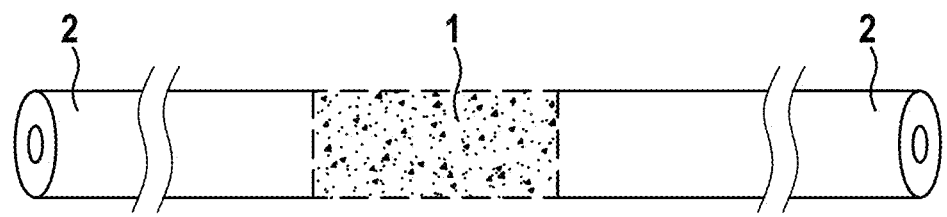
FIG. 5 is a representation of an arrangement according to the invention in the form of an open-cell drainage tube.

FIG. 5 is a representation of an arrangement according to the invention in the form of an open-cell drainage tube. Open-cell fluid-collecting segment 1 or contact element 1 is located in the center of a tubular fluid-communicating element 2.

Figure 6:
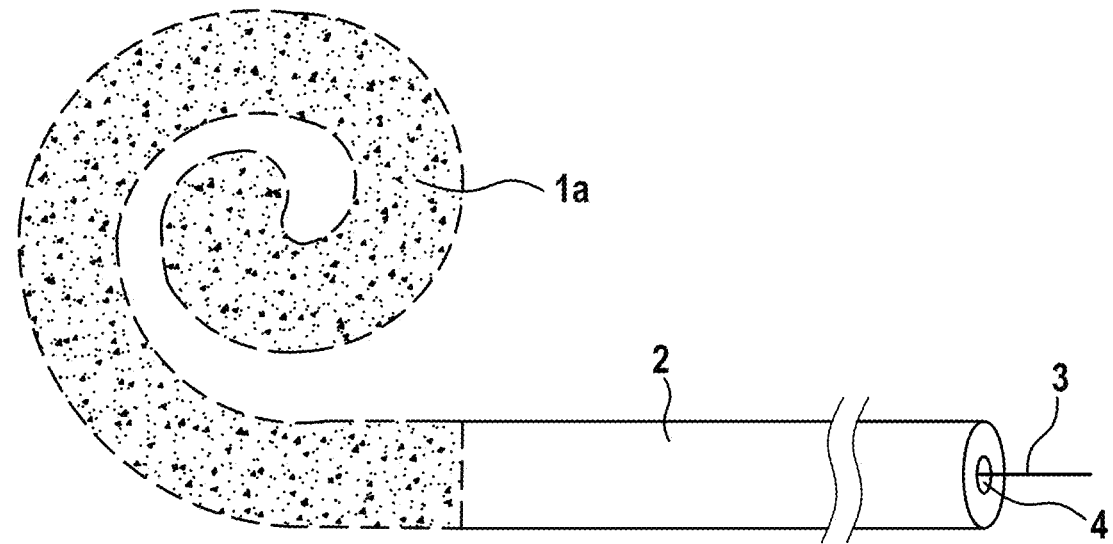
FIG. 6 is a representation of an arrangement according to the invention in the form of open-cell drainage tube.

FIG. 6 is a representation of an arrangement according to the invention in the form of open-cell drainage tube. A spirally curved open-cell fluid-collecting segment 1a is located at the distal end of tubular fluid-communicating element 2. A guide wire 3 is inserted into a fluid-conductive channel 4.

Figure 7:
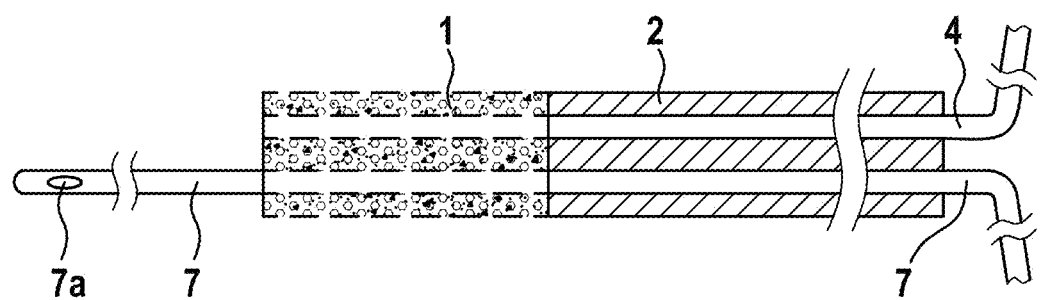
FIG. 7 is a longitudinal sectional view of an arrangement according to the invention in the form of an open-cell drainage tube.

FIG. 7 is a longitudinal sectional view of an arrangement according to the invention in the form of an open-cell drainage tube. Open-cell fluid-collecting segment 1 or contact element 1 is located at the distal end of tubular fluid-communicating element 2. A tube 7 having a perforation 7a at its end passes through. It can be used as a feeding tube. A channel 4 is fluid-conductively connected to fluid-collecting segment 1.

Figure 7A:
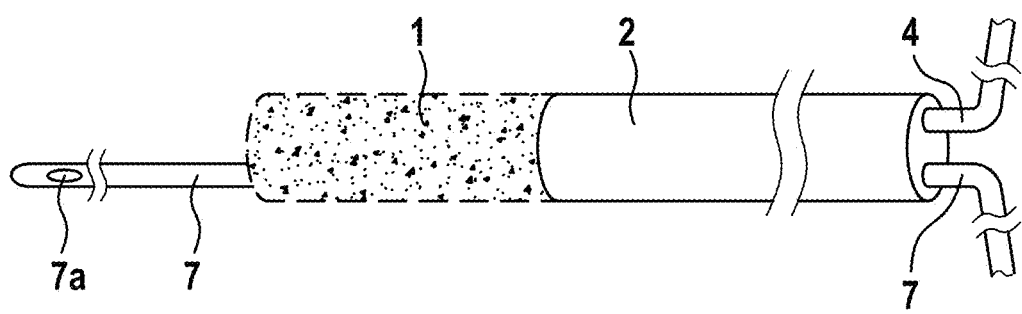
FIG. 7a is an additional representation of FIG. 7.

FIG. 7a is an additional representation of FIG. 7. Open-cell fluid-collecting segment 1 or contact element 1 is located at the distal end of tubular fluid-communicating element 2. A tube 7 having a perforation 7a at its end passes through. It can be used as a feeding tube. A channel 4 is fluid-conductively connected to fluid-collecting segment 1.

FIGS. 8a-8f are representations of the open-cell drainage tube. Various variants of the points of transition from fluid-collecting segment 1 to fluid communicating element 2 are represented.

Figure 8A:
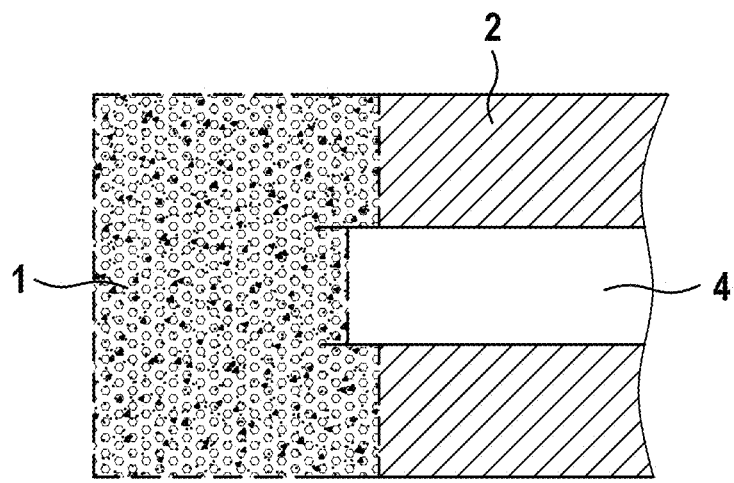
FIGS. 8a-8f are representations of the open-cell drainage tube.

FIG. 8a is a longitudinal sectional view of the transition from fluid-collecting segment 1 to fluid-communicating element 2. Open-cell fluid-collecting segment 1 or contact element 1 is continuously connected to fluid-communicating element 2. In fluid-communicating element 2, a fluid-conductive channel 4 is provided.

Figure 8B:
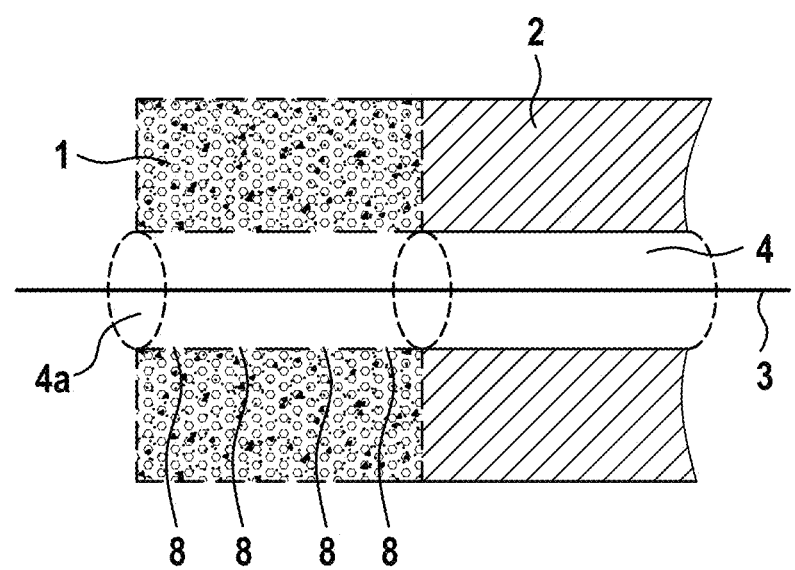

FIG. 8b is a longitudinal sectional view of the transition from fluid-collecting segment 1 to fluid-communicating element 2. Open-cell fluid-collecting segment 1 or contact element 1 is continuously connected to fluid-communicating element 2. In fluid-communicating element 2, a fluid-conductive channel 4 is located, which is conducted on as a negative pressure-stable tube in fluid-collecting segment 1 and is fluid-conductively connected to fluid-collecting segment 1 by lateral perforations 8. A guide wire 3 is inserted into channel 4.

Figure 8C:
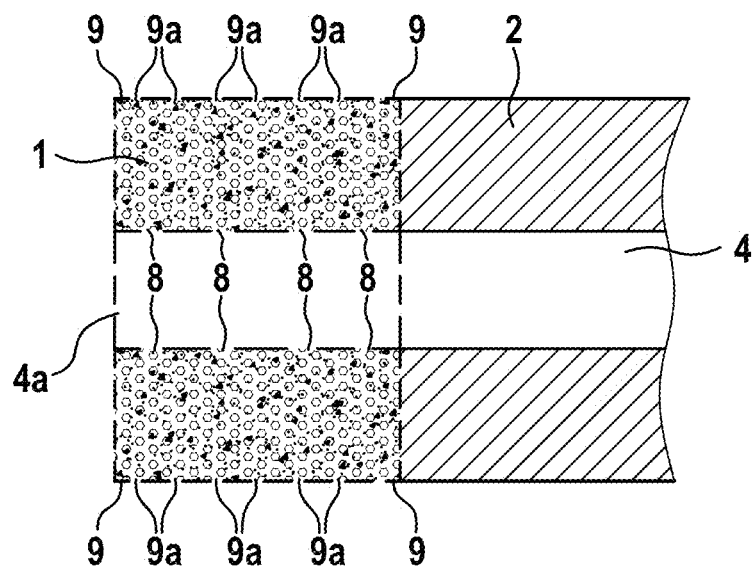

FIG. 8c is a longitudinal sectional view of the transition from fluid-collecting segment 1 to fluid-communicating element 2. Open-cell fluid-collecting segment 1 or contact element 1 is continuously connected to fluid-communicating element 2. In fluid-communicating element 2, a fluid-conductive channel 4 is located, which is conducted on as a negative pressure-stable tube in fluid-collecting segment 1 and is fluid-conductively connected to fluid-collecting segment 1 by lateral perforations 8. Fluid-collecting segment 1 is covered by a film 9 having fluid-conductive perforations 9a. Film 9 merges continuously into fluid-communicating element 2. The exterior covering of film 9 is intended to bring about improved slidability of the drain to improve placement and removal.

Figure 8D:
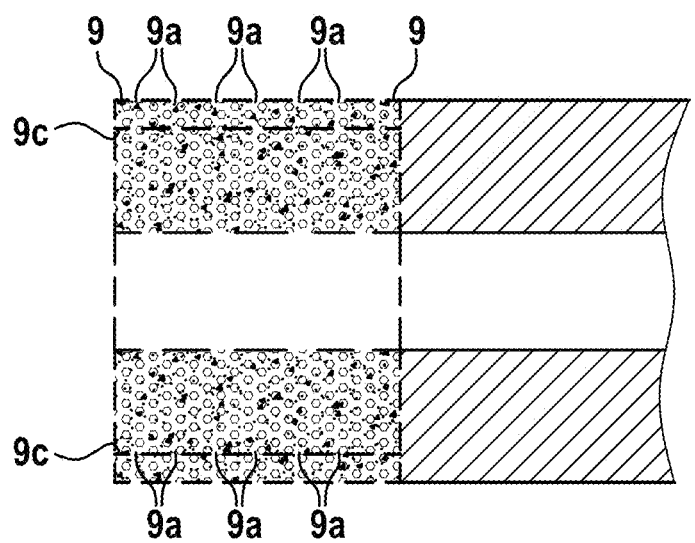

FIG. 8d corresponds to the longitudinal sectional view in FIG. 8c. In addition, open-cell fluid-collecting segment 1 or contact element 1 is provided and/or permeated by an additional film 9c having fluid-conductive perforations 9a.

Figure 8E:
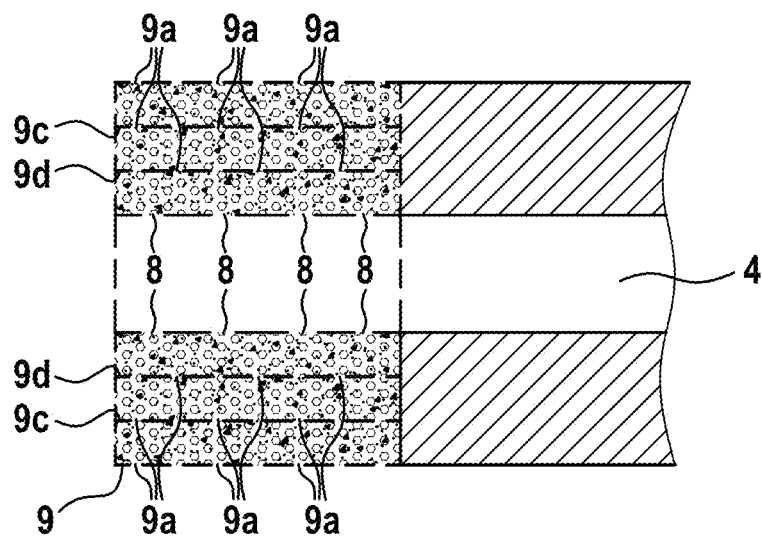

FIG. 8e corresponds to the longitudinal sectional view in FIG. 8d. In addition, open-cell fluid-collecting segment 1 or contact element 1 is provided and/or permeated by an additional film 9d having fluid-conductive perforations 9a. The multilayer film design increases the tensile strength. The design of open-cell multilayer films 9, 9c, 9d is intended to achieve maximum fluid conduction in conjunction with a small drain diameter.

Figure 8F:
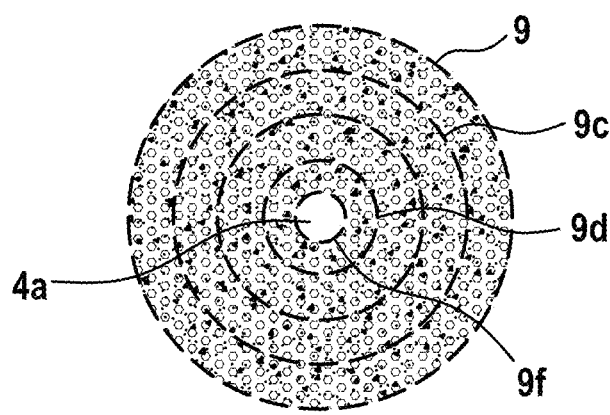

FIG. 8f corresponds to the cross sectional view of a drain having four tubular film layers 9, 9c, 9d, 9f and being provided with central fluid-conductive channel 4a.

Figure 9:
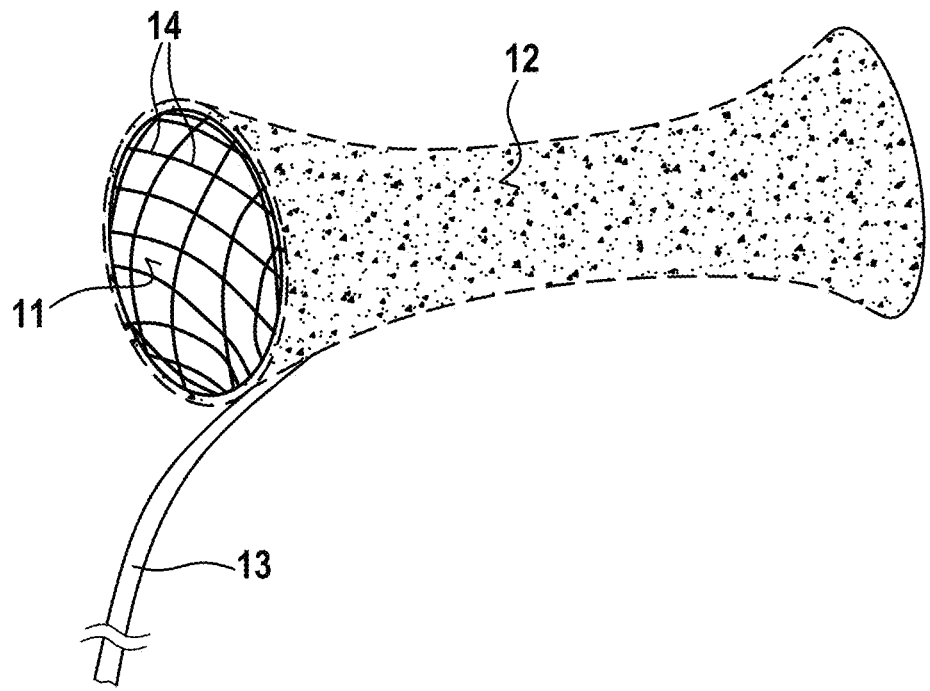
FIG. 9 is a plan view of a self-expanding metal or plastic mesh stent.

FIG. 9 is a plan view of a self-expanding metal or plastic mesh stent, which consists of a self-expanding metal or plastic wire mesh 14. The stent is completely jacketed by a unilaterally open-celled film 9 or a contact element 1, the outside 12 of which has an open-cell structure and the inside 11 of which that is open cell-free abuts metal or plastic mesh wires 14. The outer open-cell surface is fluid-conductively connected to drainage tube 13. Both ends are flared funnel-like.

Figure 10:
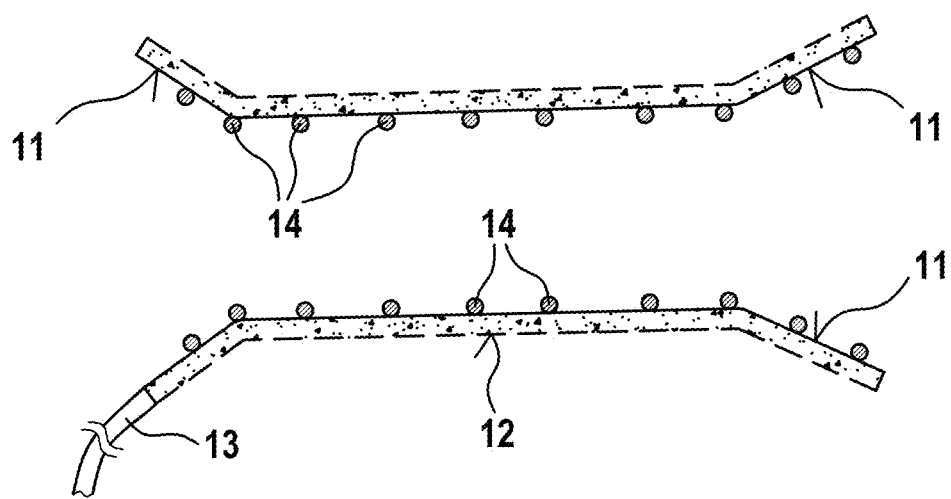
FIG. 10 is a longitudinal sectional view of FIG. 9.

FIG. 10 is a longitudinal sectional view of FIG. 9. Surface side 11 of the film, situated inside, is open cell-free and abuts the metal or plastic mesh wires 14. Open-cell surface side 12 of the film is situated outside and is fluid-conductively connected to a tubular drain 13. Both ends are flared funnel-like.

Figure 11:
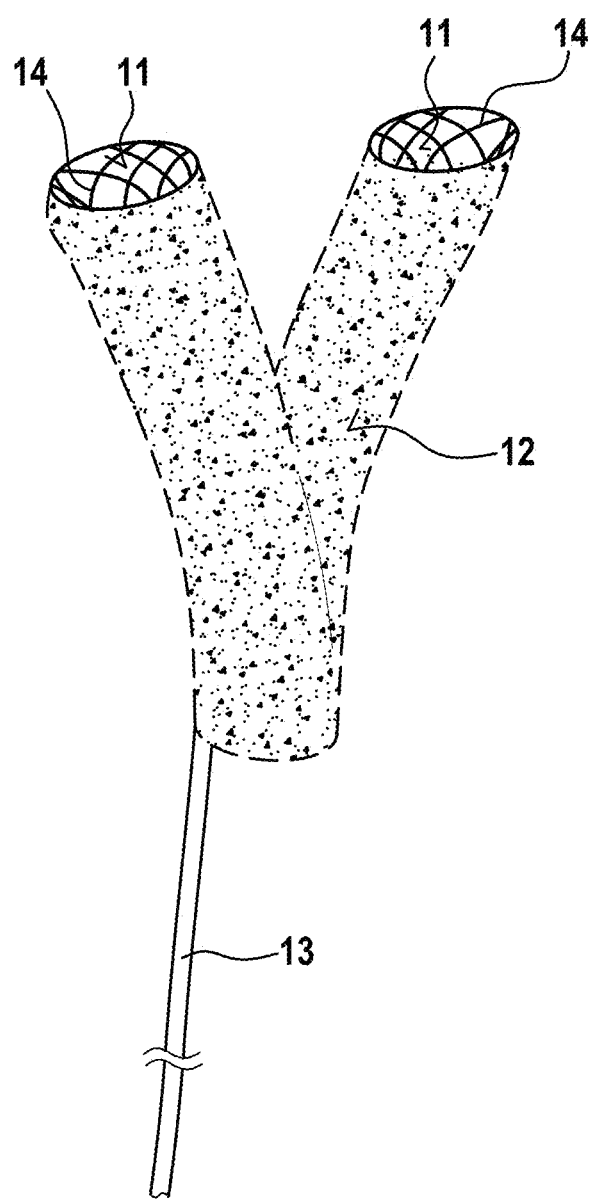
FIG. 11 is a plan view of a self-expanding Y-shaped metal or plastic mesh stent.

FIG. 11 is a plan view of a self-expanding Y-shaped metal or plastic mesh stent, which consists of a self-expanding metal or plastic wire mesh 14. The stent is completely jacketed in unilaterally open-celled film, the outside 12 of which has an open-cell structure and the inside 11 of which that is open cell-free abuts the metal or plastic mesh wires 14. The outer open-cell surface 12 is fluid-conductively connected to a drainage tube 13. This embodiment of a Y-shaped stent intends illustrate the possibility of its application in the tracheobronchial system in an exemplary manner.

Figure 12:
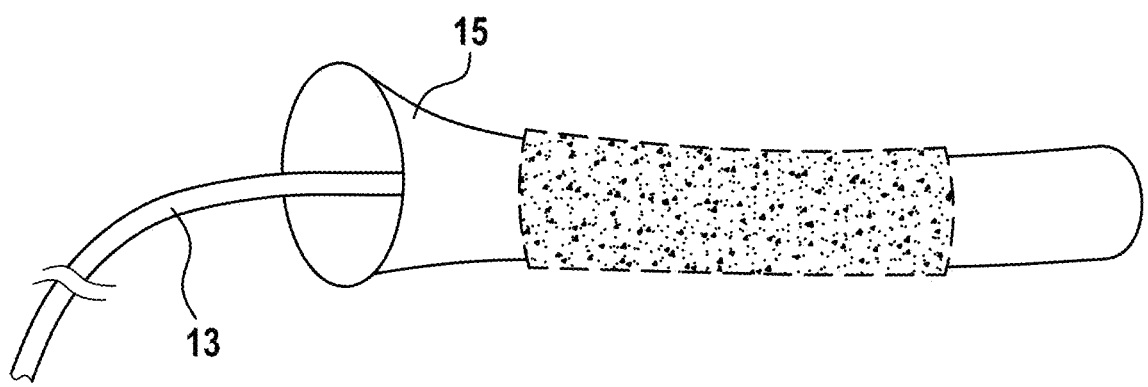
FIG. 12 is a plan view of a tubular tubus.

FIG. 12 is a plan view of a tubular tubus, the wall of which in the center portion of the tubus has a circular unilaterally open-celled structure. The externally visible open-cell structure of the wall is marked 12. It is fluid-conductively connected to a tubular drainage line 13, which is brought up from the inside of the tubus. One end is flared funnel-like.

Figure 13:
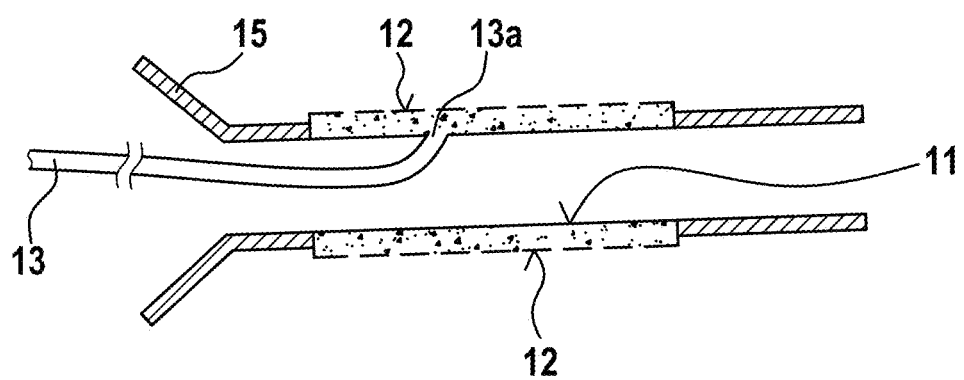
FIG. 13 is a longitudinal sectional view of FIG. 12.

FIG. 13 is a longitudinal sectional view of FIG. 12 The wall of the tubus is designed unilaterally open. The inside 11 of the wall is open cell-free, the outer wall 12 has open cells in the center part of the tubus. From inside, by way of a perforation 13a, a drainage line 13, fluid-conductive, is brought up to the outside. One end is flared funnel-like.

Figure 14:
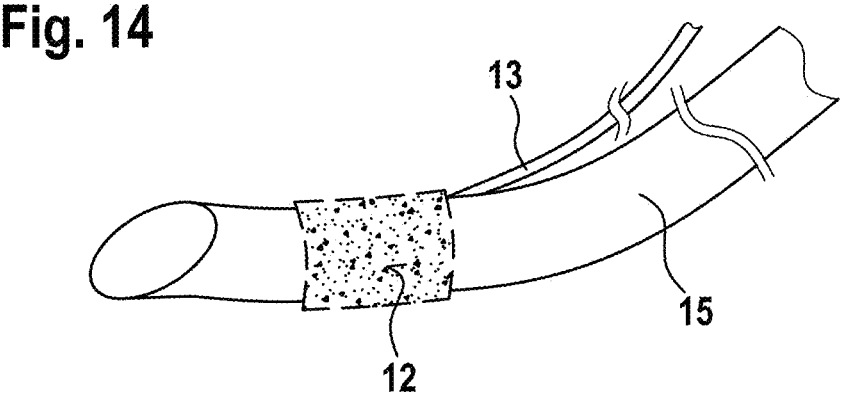
FIG. 14 is a plan view of an intubation tubus according to one embodiment.

FIG. 14 is a plan view of a special form of a tubus. It involves an intubation tubus. In its distal portion, tubus tube 15 is enclosed by an open-cell film. A fluid-conductive tube 13 leads to open-cell surface 12.

Figure 15:
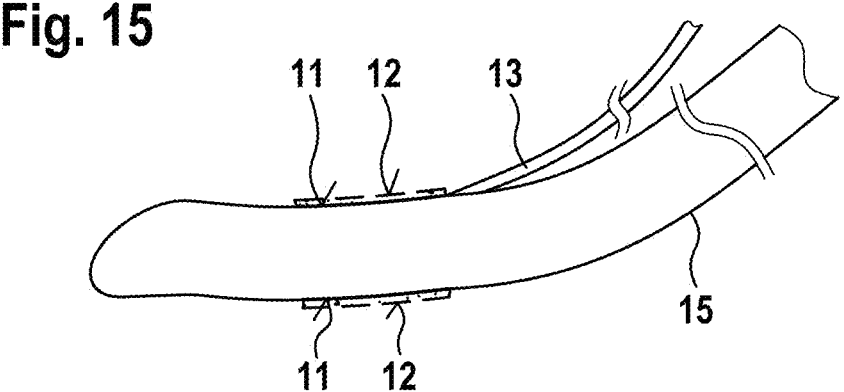
FIG. 15 is a longitudinal sectional view of FIG. 14.

FIG. 15 is a longitudinal sectional view of FIG. 14. The distal portion of tubus tube 15 is enclosed by an open-cell film. 12 is the open-cell surface situated outside. Open cell-free surface 11 abuts tubus tube 15. A fluid-conductive connection to a tube 13 exist.

Figure 16:
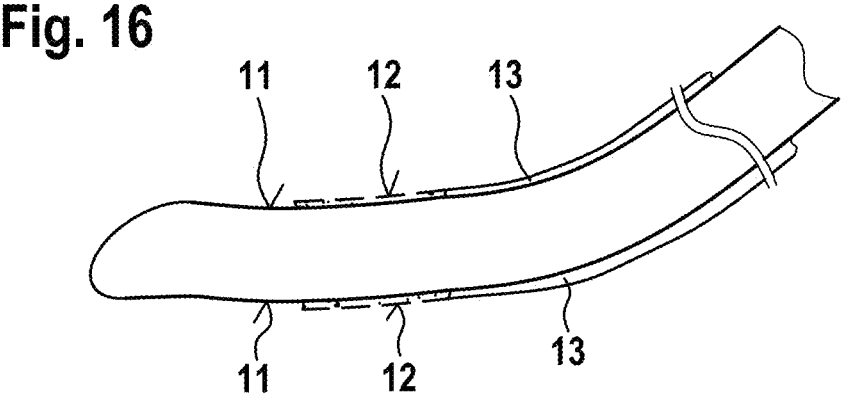
FIG. 16 is a longitudinal sectional view of an intubation tubus according to a second embodiment.

FIG. 16 is a longitudinal sectional view of a tubus, in which the wall of the tubus per se is open-celled 12 on the outside and open cell-free 11 toward the inside. Situated in the wall are the tubular drainage lines 13, which are fluid-conductively connected to the open-cell surface.

Figure 17:
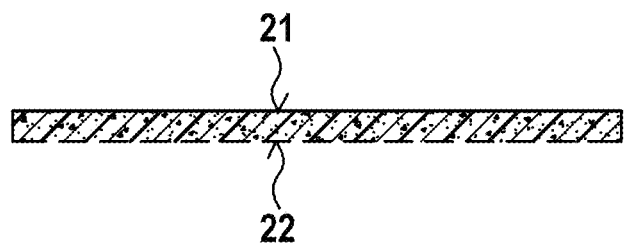
FIG. 17 is a cross-sectional view of a unilaterally open-celled film.

FIG. 17 is a cross-sectional view of a unilaterally open-celled film having an open cell-free surface side 21 and an open-cell surface side 22.

Figure 18:
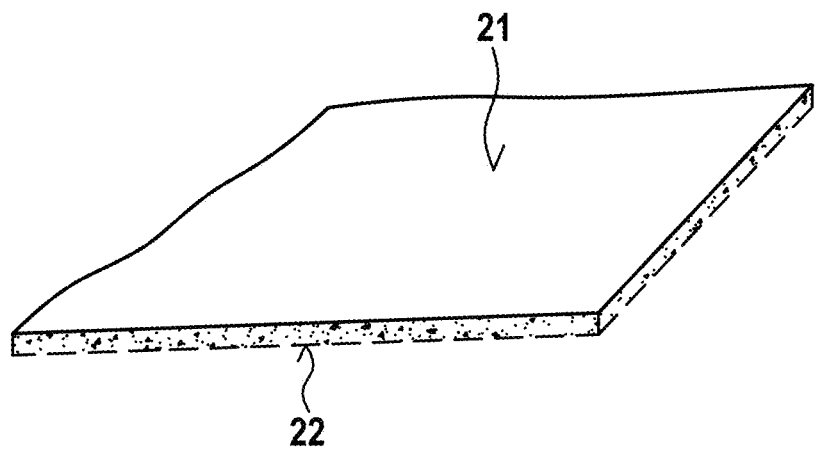
FIG. 18 is a plan view of a unilaterally open-celled film.

FIG. 18 is a plan view of a unilaterally open-celled film having an open cell-free surface side 21 and an open-cell surface side 22. The film is cut to size to be rectangular.

Figure 19:
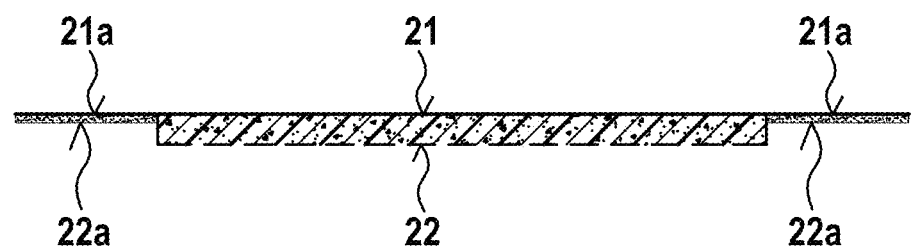
FIG. 19 is a cross-sectional view of a unilaterally open-celled film according to a first embodiment.

FIG. 19 is a cross-sectional view of a unilaterally open-celled film having an open cell-free surface side 21 and an open-cell surface side 22. In the peripheral area of the film, both the open-cell surface side 21a and the open-cell surface side 22a are open cell-free. Peripheral area 21a and/or 22a can be provided with an adhesive so that the film in peripheral area 21a, 22a is closed off gas and air-tight when they are glued down and/or glued to each other.

Figure 20:
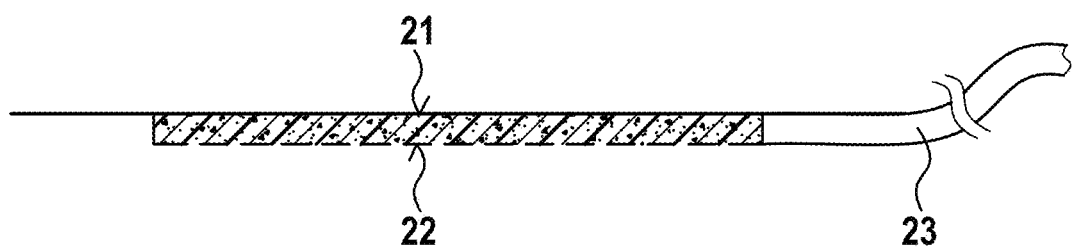
FIG. 20 is a cross-sectional view of a unilaterally open-celled film according to a second embodiment.

FIG. 20 is a cross-sectional view of a unilaterally open-celled film having an open cell-free surface side 21 and an open-cell surface side 22. To open-cell surface side 22, fluid-conductively, a tubular fluid-communicating means 23 is connected, which is brought up to open-cell surface side 22 from the outside and fluid-conductively connected to it.

Figure 21:
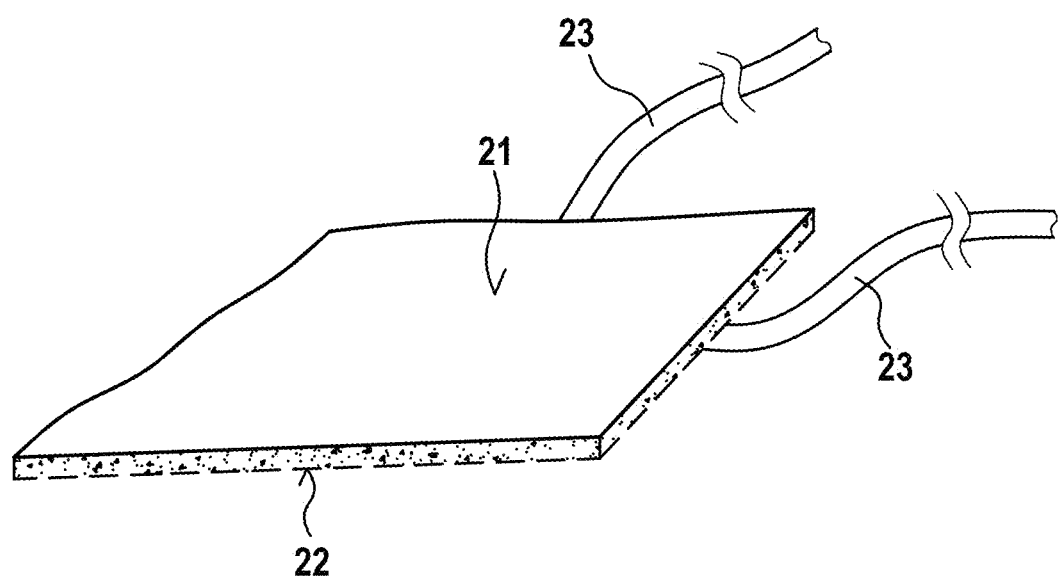
FIG. 21 is a plan view of a unilaterally open-celled film according to a third embodiment.

FIG. 21 is a plan view of a unilaterally open-celled film having an open cell-free surface side 21 and an open-cell surface side 22. To open-cell side 22, fluid-conductively, two tubular fluid-communicating means 23 are connected, which are brought up to open-cell surface side 22 from the outside and fluid-conductively connected to it.

Figure 22:
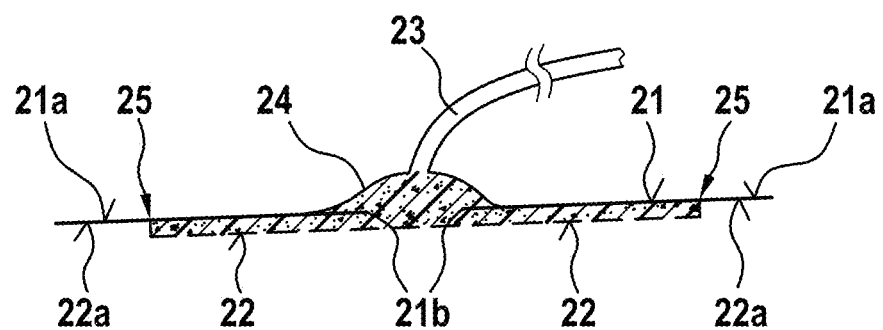
FIG. 22 is a cross-sectional view of a unilaterally open-celled film according to a fourth embodiment.

FIG. 22 is a cross-sectional view of a unilaterally open-celled film having an open cell-free surface side 21 and an open-cell surface side 22. By means of a pelotte 24, the tubular fluid-communicating means 23 is fluid-conductively connected, by way of a port 21b of the open cell-free surface side 21, to open-cell surface side 22. 25 marks the transition, where, in the peripheral area, both surface sides merge into an open cell-free surface (21a and 22a).

Figure 23:
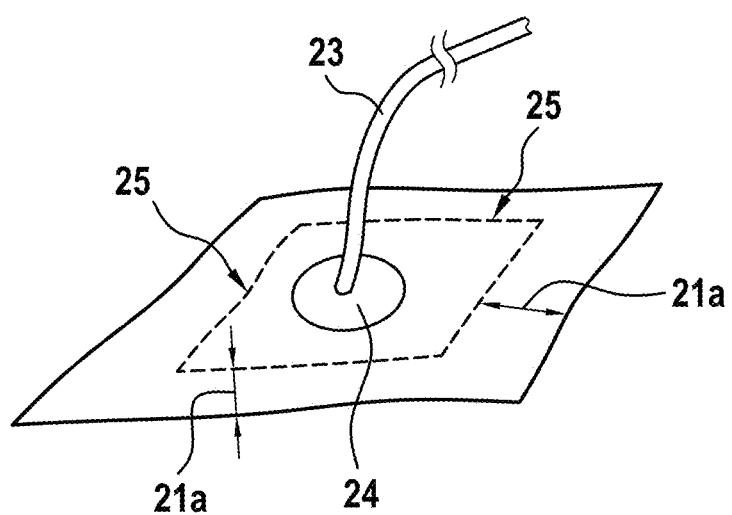
FIG. 23 is a plan view of FIG. 22.

FIG. 23 is a plan view of FIG. 22. The fluid-conductive pelotte 24 is centrally attached to a rectangular film. In peripheral area 21a, the film is bilaterally open cell-free. The transition to the open-cell surface (not visible here) is marked 25.

Figure 24:
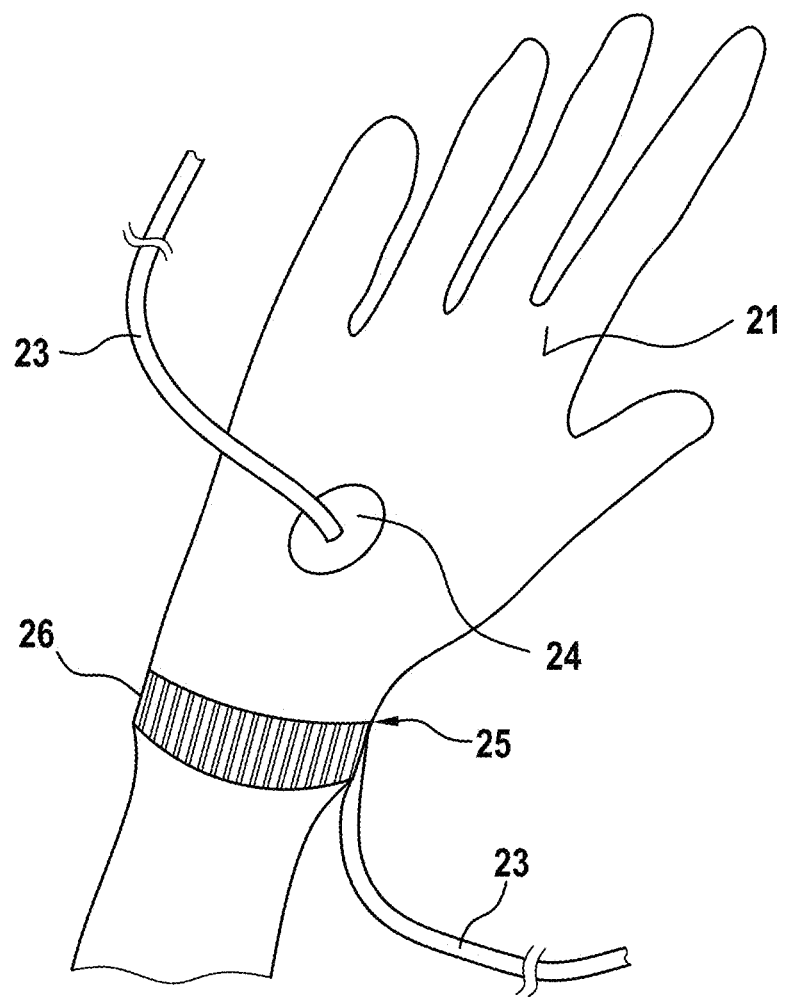
FIG. 24 is an exemplary representation of a film adapted to a type of clothing.

FIG. 24 is an exemplary representation of a film adapted to a type of clothing, in this case in glove form. On the outside is the open cell-free film side 21, tubular fluid-communicating means 23 are conducted to the open-cell film side (invisible, situated inside), one of them by way of a pelotte 24. The termination 26 of the glove is glue-bonded to the skin, the inner invisible transition to the open-cell side of the peripheral area is marked 25.

REFERENCE LIST 1, 1a Fluid-Collecting Segment/Contact Element
2 Fluid-Communicating Element
3 Guide Wire
4, 4a, 4b, 5 Channel
6 Wirelike Thread
6a Winding Curve
7 Tube
7a, 8, 9a, 13a Perforations
9, 9c, 9d, 9f Film
11 Inside/Surface Sides of the Film Situated Inside
12 Outside/Surface Sides of the Film Situated Outside/Exterior Wall
13 Drainage Tube/Drainage Line
14 Metal or Plastic Mesh Wires/Metal or Plastic Wire Mesh
15 Tubus Tube
21 Surface Side of the Film (Open Cell-Free)
22 Surface Side of the Film (Open-Cell)
21a, 22a Peripheral Area
21b Port
23 Fluid-Communicating Means
24 Pelotte
25 Transition
26 Termination (Glove)

What is claimed and desired to be secured by Letters Patent is as follows:

1. A negative pressure treatment arrangement comprising:
a self-expanding mesh stent;
a gas and fluid-impermeable membrane, wherein a first side of the membrane comprises an open-cell material, wherein a second side of the membrane does not comprise an open-cell material, wherein the self-expanding mesh stent is jacketed by the membrane such that the first side of the membrane is on the outside of the jacketed stent; and
a fluid-communicating element connected to the open-cell material of the first side of the membrane, wherein when the fluid-communicating element is connected to a vacuum-generating system, a negative pressure of up to 200 mm Hg is capable of being applied to the open-cell surface of the film.

2. The negative pressure treatment arrangement of claim 1, wherein cells of the open-cell material are mesh, nub, finger, or channel-shaped.

3. The negative pressure treatment arrangement of claim 1, wherein a cell size of cells of the open-cell material of the first side is between 200 μm and 1000 μm.

4. The negative pressure treatment arrangement of claim 1, wherein the stent is a self-expanding Y-shaped mesh stent.

5. The negative pressure treatment arrangement of claim 1, wherein the fluid-communicating element comprises a plurality of negative pressure-stable tubes.

6. The negative pressure treatment of claim 1, wherein the open-cell material of the first side comprises open-cell polyurethane foam.

7. The negative pressure treatment of claim 1, wherein the open-cell material of the first side comprises open-cell dual or multilayer perforated films.

8. The negative pressure treatment of claim 7, wherein each film of the open-cell dual or multilayer perforated films is spaced in such a way using spacers from other films of the open-cell dual or multilayer perforated films that each film of the open-cell dual or multilayer perforated films does not have any direct areal contact with other films of the open-cell dual or multilayer perforated films.

9. The negative pressure treatment of claim 8, wherein each film of the open-cell dual or multilayer perforated films are provided with a plurality of perforations.

* * * * *